United States Patent
Ramesh Kumar et al.

(10) Patent No.: US 10,959,612 B2
(45) Date of Patent: Mar. 30, 2021

(54) METHOD FOR CLASSIFYING THE CATARACT OF AN EYE

(71) Applicant: Carl Zeiss Meditec AG, Jena (DE)

(72) Inventors: Akhil Ramesh Kumar, Oberkochen (DE); Tobias Bühren, Magdala (DE); Joao Emanuel Goncalves Bras, Hannover (DE); Manfred Dick, Gefell (DE); Ferid Bajramovic, Mamming (DE); Martin Volkwardt, Stadtroda (DE)

(73) Assignee: Carl Zeiss Meditec AG, Jena (DE)

( * ) Notice: Subject to any disclaimer, the term of this patent is extended or adjusted under 35 U.S.C. 154(b) by 463 days.

(21) Appl. No.: 15/745,902

(22) PCT Filed: Jul. 6, 2016

(86) PCT No.: PCT/EP2016/066039
§ 371 (c)(1),
(2) Date: Jan. 18, 2018

(87) PCT Pub. No.: WO2017/016834
PCT Pub. Date: Feb. 2, 2017

(65) Prior Publication Data
US 2018/0206717 A1 Jul. 26, 2018

(30) Foreign Application Priority Data
Jul. 24, 2015 (DE) .................. 10 2015 009 641.9

(51) Int. Cl.
*A61B 3/14* (2006.01)
*A61B 3/10* (2006.01)
(Continued)

(52) U.S. Cl.
CPC ............ *A61B 3/102* (2013.01); *A61B 3/1176* (2013.01); *A61F 9/00745* (2013.01); *A61F 2009/00887* (2013.01); *A61F 2009/00897* (2013.01)

(58) Field of Classification Search
CPC ........... A61B 3/14; A61B 3/103; A61B 3/113; A61B 3/1208; A61B 3/1225; A61B 3/024; A61B 3/032; A61B 3/18; A61B 3/1015
(Continued)

(56) References Cited

U.S. PATENT DOCUMENTS

| 8,360,577 | B2 | 1/2013 | Nixon | |
|---|---|---|---|---|
| 2010/0118266 | A1* | 5/2010 | Nixon | A61B 3/1173 351/206 |

(Continued)

FOREIGN PATENT DOCUMENTS

| AU | 2015 203 440 A1 | 7/2015 |
|---|---|---|
| DE | 10 2005 026 371 A1 | 12/2006 |

(Continued)

OTHER PUBLICATIONS

PCT International Preliminary Report on Patentability and Written Opinion for International Application No. PCT/EP2016/066039, dated Feb. 8, 2018, 8 pages.

(Continued)

*Primary Examiner* — Dawayne Pinkney
(74) *Attorney, Agent, or Firm* — Patterson Thuente Pedersen, P.A.

(57) ABSTRACT

A method for classifying a cataract of an eye to determine parameters for pre-setting phaco-treatment instruments. OCT-based measurements are realized. The OCT-based scans are analysed using imaging technology and the local distribution of the cataract is determined. The cataract is classified on the basis of comparison values and the local (Continued)

distribution and classification of the cataract are used to identify parameters for pre-setting phaco-treatment instruments. Even though the proposed method for classifying the cataract of an eye is provided for determining parameters for pre-setting phaco-treatment instruments, it should equally also be used for determining parameters for pre-setting treatment instruments based on fs-lasers.

26 Claims, 2 Drawing Sheets

(51) Int. Cl.
*A61B 3/02* (2006.01)
*A61B 3/00* (2006.01)
*A61B 3/117* (2006.01)
*A61F 9/007* (2006.01)
*A61F 9/008* (2006.01)

(58) Field of Classification Search
USPC ............... 351/206, 200, 205, 209–210, 218, 351/221–223, 245–246
See application file for complete search history.

(56) References Cited

U.S. PATENT DOCUMENTS

| 2013/0226072 | A1 | 8/2013 | Kraus et al. |
| 2013/0265542 | A1* | 10/2013 | Frey ........................ A61F 9/008 351/206 |
| 2016/0302660 | A1* | 10/2016 | Buhren ................ A61B 3/0025 |
| 2016/0302971 | A1* | 10/2016 | Morley ............... A61F 9/00825 |
| 2016/0360962 | A1* | 12/2016 | Okamoto .................. G06T 7/12 |
| 2018/0146850 | A1* | 5/2018 | Fernandes Da Cunha-Vaz .......... A61B 3/102 |

FOREIGN PATENT DOCUMENTS

| DE | 10 2012 019 474 A1 | 4/2014 |
| EP | 1 731 086 A2 | 12/2006 |
| EP | 1 835 872 A1 | 9/2007 |
| WO | WO 2006/060423 A1 | 6/2006 |

OTHER PUBLICATIONS

PCT International Search Report and Written Opinion for International Application No. PCT/EP2016/066039, dated Nov. 24, 2016, 11 pages.
English translation of PCT International Search Report for International Application No. PCT/EP2016/066039, dated Nov. 24, 2016, 3 pages.
DE Search Report for 10 2015 009 641.9, dated Apr. 19, 2016, 9 pages.
L.T. Chylack, et al.; "Lens Opacities Classifications System LOCS III", Arch Ophthalmol, vol. 111, Jun. 1993, 831-836.
J. Belikova, et al.; "Correlation of Age-Related Cataract Density Graded by the Scheimpflug Imaging System with Visual Function and Phacoemulsification Energy"; Coll. Antropol. 37 (2013) Suppl. 1: 25-30.
Nixon, DR; "Preoperative cataract grading by Scheimpflug imaging and effect on operative fluidics and phacoemulsification energy"; Journal of Cataract and Refractive Surgery Feb. 2010; vol. 36 (2), pp. 242-246.
A. L. Wong, et al.; "Quantitative assessment of lens opacities with anterior segment optical coherence tomography", British Journal of Ophthalmology Jan. 2009; vol. 93 (1), pp. 61-65.
Potsaid, Benjamin [et al.]: Ultrahigh speed 1050nm swept source/ Fourier domain OCT retinal and anterior segment imaging at 100,000 to 400,000 axial scans per second. In: Optics Express, vol. 18, 2010, No. 19, S. 20029-20048.
Smith, Martin R: Cataract, macular characteristics and assessing lens opacities. 2014, Doktorarbeit, Aston University.

* cited by examiner

METHOD FOR CLASSIFYING THE CATARACT OF AN EYE

RELATED APPLICATIONS

This application is a National Phase entry of PCT Application No. PCT/EP2016/066039 filed Jul. 6, 2016 which application claims the benefit of priority to German Application No. 10 2015 009 641.9, filed Jul. 24, 2015, the entire disclosures of which are incorporated herein by reference.

FIELD OF THE INVENTION

The present invention relates to a method for classifying a cataract of an eye for determining parameters for presetting phaco-treatment machines.

BACKGROUND

The cataract, also referred to as a gray star, is a disease in which case the vision becomes impaired due to a clouding of the eye lens. It is one of the most frequent eye diseases in old age. In an advanced stage, the clouding of the eye lens can be clearly recognized as a gray coloration. The clouded lens can be surgically removed in most cases and replaced with an artificial lens implant. The cataract varies in its density or hardness depending on the stage it has reached.

Basically, there are two different approaches in cataract surgery.

In the method referred to as phacoemulsification the front of the capsular bag is opened and the lens is disintegrated and suctioned by application of ultrasound while preserving the remaining capsule. Then an artificial lens is inserted into the empty capsular bag. These intraocular lenses consisting of elastic material are inserted in a folded or rolled state, after which they unfold in the capsular bag and center and fix themselves in place by use of two elastic straps (haptics/feel).

In the case of phacoemulsification, along with the ultrasound fragmentation of the lens, its suctioning and the rinsing of the lens capsular bag are also realized via the probe to be inserted into the eye. The control of the individual functions is performed intraoperatively by the operator via a control panel.

In the case of suctioning the eye lens that has been fragmented by application of ultrasound, the resulting cavity of the capsular bag is simultaneously filled with fluid. This serves a twofold purpose: rinsing and maintaining the intraocular pressure and the volume.

All of the parameters required for phacoemulsification, such as ultrasound performance, vacuum, rinse flow and pressure must be set in advance via the machine user interface. The type of respective eye, in particular its length (short, normal or long) also has an influence on the parameters that are to be set.

Both the degree of the cataract as well as the type of eye of the patient are to be considered in the setting of these parameters. Not least, also the personal experiences of the respective operator and said operator's surgical technique have a significant influence on the parameters to be set.

In the normal case the phaco-treatment instruments will be set up by a nurse on the basis of the treatment programs preset for the various types of cataract. The nurse must check the patient data and the device settings in accordance with the specifications of the operator, which as a rule increases the demands on the workflow.

In the process, there can be delays or errors on the part of the nurse or on the part of the operator.

According to the known prior art, the parameters to be set for phaco-treatment instruments are currently based primarily on the visual manual assessment of the cataract types and degree of cataracts.

In order to prevent the reproducibility of the parameters as well as potential individual errors in the visual, manual assessment, L. T. Chylack and others developed the classification tool "LOCS III". The classification tool "LOCS III" described in [1] is based on a rather time consuming manual process with a slit lamp.

According to the prior art, additional solutions are known for diagnosing the cataract density which, in contrast to the classification tool "LOCS III", are based on Scheimpflug imaging technology.

J. Belikova and others demonstrate in [2] that it is possible on the basis of a 3D lens densitometry to determine parameters with Scheimpflug light section technology and use them for presetting phaco-treatment machines.

Further, D. R. Nixon and others show that it is possible for one thing to classify cataracts with the help of Scheimpflug images. For another thing, the preoperative setting of the parameters can lead to the optimization of the phaco-treatment and shorten the treatment period.

In this connection, DE 1-2005 026 371 A1 discloses a method in which a cataract analysis can be performed with a Scheimpflug camera system. The inventive method involves the basic principle of using a slit projection device and a Scheimpflug recording device that can be rotated together around an axis. Three-dimensional information can be obtained through photographs in various levels of the eye. With the inventive method it is possible to examine individual components of the eye through data analysis. According to one variant, the examination method can be used to determine the three-dimensional geometry of the cataract. However, no provision is made for the classification of the cataract or generation of default values for a later phaco-treatment.

U.S. Pat. No. 8,360,577 B2 also describes an optical imaging system in which the scattering image taken with a Scheimpflug camera of the eye lens is three-dimensionally analyzed. However, in the case of this solution each newly registered scattering image is compared to a set of previously recorded scattering images that have been assigned to a cataract level and then classified in the corresponding degree of cataract.

However, not only images according to the Scheimpflug principle can be used for determining the cataract density. This discovery was made by A. L. Wong and documented in [4]. In this article, studies on cataract density were conducted with the help of optical coherence tomography (OCT) and it turns out that the determined data are comparable to the degree of cataracts determined according to the classification tool "LOCS III".

While in the case of phacoemulsification the opening of the front surface of the capsular bag and the fragmentation of the lens are manually performed by the operator, in the method referred to as laser-phaco this occurs with the help of a femtosecond laser (fs laser for short). In the case of an exact dosing of the laser energy, frequently the use of ultrasound probes following the phacoemulsification can be completely dispensed with.

REFERENCES

[1] L. T. Chylack, et al.; "Lens Opacities Classifications System LOCS III", Arch Ophthalmol, Vol. 111, June 1993, 831-836

[2] J. Belikova, et al.; "Correlation of Age-Related Cataract Density Graded by the Scheimpflug Imaging System with Visual Function and Phacoemulsification Energy"; Coll. Antropol. 37 (2013) Suppl. 1:25-30

[3] Nixon, D R; "Preoperative cataract grading by Scheimpflug imaging and effect on operative fluidics and phacoemulsification energy"; Journal Of Cataract And Refractive Surgery 2010 February; Vol. 36 (2), pp. 242-246

[4] A. L. Wong, et al.; "Quantitative assessment of lens opacities with anterior segment optical coherence tomography", British Journal Of Ophthalmology 2009 January; Vol. 93 (1), pp. 61-65,

SUMMARY OF THE INVENTION

The advantages of the femtosecond laser cataract operation can be seen in the essentially more precise incision and above all the gentler fragmentation of the eye lens. Not least, among other things also the sensitive inner layer of the cornea, the endothelium, is protected.

According to the prior art in this field, there are no solutions known that make possible an (automatic) presetting of phaco-treatment machines for a surgical intervention.

Although the following aspects have an increasing significance above all in the case of the optical assessment of the degree of cataract of the eye lens, said aspects have thus far not been taken into consideration at all:
 different degree of hardness from the core to the cortex of the eye lens,
 dependency of degree of hardness on the wavelength used and
 dependency of the degree of hardness on the detected scattering angles.

The present invention addresses the problem of developing a method for classifying the cataract of an eye which makes possible a simple and reliable classification and the generation of parameters for pre-setting phaco-treatment machines, wherein the geometry is to be considered as biometry of the respective eye. Manual or automatic setting of the phaco-treatment machines should make the treatment safer and faster, as well as minimizing the burden of the patient.

This problem is solved by the inventive method for classifying the cataract of an eye for determining the parameters for pre-setting phaco-treatment machines by the fact that along with keratometric measurements, in addition OCT measurements are realized, the required biometric data are determined from the keratometric and the OCT-based measurements for a phaco-treatment, the OCT-based scans are analyzed using imaging technology and the local distribution of the cataract is determined, classified with the aid of comparison values and parameters for the pre-setting of phaco-treatment machines are determined from the biometric data, the local distribution and the classification of the cataract.

Although the proposed method for classification of the cataract of an eye for the determination of parameters is provided for pre-setting phaco-treatment machines, it should likewise be used for determining parameters for pre-setting treatment machines that are based on fs lasers.

BRIEF DESCRIPTION OF THE DRAWINGS

In the following the invention will be described in greater detail based on exemplary embodiments. The figures show the following.

DETAILED DESCRIPTION

In the case of the inventive method for classifying a cataract of an eye for determining parameters for pre-setting of phaco-treatment machines, OCT-based measurements are realized, the OCT-based scans are analyzed using imaging technology and the local distribution of the cataract is determined, the cataract is classified on the basis of comparison values and parameters for pre-setting phaco-treatment machines are determined from the local distribution and the classification of the cataract.

In accordance with the invention, in the case of the method the required biometric data for a phaco-treatment can be determined from the OCT-based measurements and parameters for pre-setting phaco-treatment machines can be used for classification of the cataract.

However, it is also possible to realize keratometric measurements along with OCT-based measurements, determine the biometric data required for a phaco-treatment from the OCT-based and the keratometric measurements and determine parameters for the pre-setting of phaco-treatment machines from the biometric data, the local distribution and the classification of the cataract.

According to a first embodiment, keratometric measurements take place in at least one, for example 6 and in another example 18 or more measurements.

With the keratometric measurement the surface curvature of the cornea of the eye as well as the corneal curves are determined. In the process, an illuminated object is set up at a known distance and the reflection of the cornea is measured in order to be able to draw conclusions about the curvature of the cornea. The precision of the determination of the surface curvature of the cornea rises logically with the number of measuring points.

Figure 1:
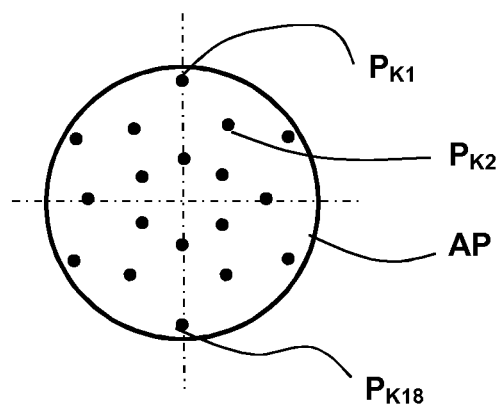
FIG. 1: shows a pupil with 18 keratometric measurement points.

To this end FIG. 1 shows an eye pupil AP with 18 keratometric measuring points $P_{K1}$ to $P_{K18}$.

According to a second embodiment, a swept source laser light source is used for the OCT-based measurements which emits short-coherent light with a wavelength between 800 nm and 1100 nm, for example 1060 nm. The OCT-based measurements have an axial resolution <25 µm and a lateral resolution <100 µm.

The optical coherence tomography is a very sensitive and rapid method for interferometric imaging, which has found widespread application in particular in the medical field and in basic research.

The swept source laser light source is a spectrally tunable light source. The OCT-based measurements are hence based on a frequency domain OCT. In the process, to achieve a suitable measuring depth in the eye and a necessary depth resolution, an axial OCT scan depth of 2 mm to 2 m, in particular 60 mm in the air as well as a spectral bandwidth of the radiation source between 3 nm and 260 nm, preferably between 10 nm and 100 nm and especially preferably between 20 nm and 40 nm are provided. Thus, in the case of a sufficient scan depth over the entire eye and in particular the lens a depth resolution of ≤25 µm in the lens tissue can be achieved, with which the substructure of the lens can be sufficiently characterized. In order to also achieve an appropriate lateral resolution of the scattering particles in the cataract lens, provision is made to design the aperture, focusing and lateral scan resolution such that the lateral resolution of the OCT biometer ≤100 µm. In accordance with the invention, that is necessary in order, in particular in addition to the good local allocation of the scattering intensities, to be able to carry out a sufficient assessment of the scattering structures. A further embodiment of a frequency domain OCT method can occur with a wide-band light source, such as e.g. a super luminescence diode (SLD), in which case the information is obtained by means of a spectrometer.

One great advantage of the OCT is the decoupling of the depth resolution from the transverse resolution. As a result, very good axial resolutions can be achieved, also in the case of limited numeric apertures. The OCT measurements based on backscattered radiation and reflection hence facilitate the generation of microscopic images of living tissue (in vivo).

One advantage of the swept source laser light source used here can be seen in the fact that the entire eye length can be recorded in only one A scan. Moreover, with the swept source-based technology, in particular in the B scan differing lateral local scattering properties of the eye lens can be resolved, which result from different cataract degrees and with which different optical and thus also mechanical properties correlate.

Thus it is possible to detect existing differences in the cataract degrees in the core and cortex of the eye lens and specify them as local distribution of the cataract. From this local distribution an average parameter can then be determined for classification of the cataract.

Figure 2:
FIG. 2: shows an OCT scan of the entire eye.

In order to detect the biometric data contained within from the OCT-based measurements, for example the eye length known image analysis methods are employed. To this end FIG. 2 shows an OCT scan of the entire eye, in which the cornea H, the eye lens AL and the retina R can be clearly recognized.

The selection of the mentioned wavelengths occurs against the background that the tissue of the human eye shows the highest transmission in the case of longer wavelengths in the near-infrared spectral range and as a result permits even the detection of the comparatively low scattering efficiency and even slight differences can be detected in the scattering behavior with high resolution. In the process, the high sensitivity of the swept source-based OCT method, approximately, 80-100 dB is very helpful. In contrast to the inventive arrangement, Scheimpflug methods use the high scattering coefficients of short-wave visible light with a high color temperature. With this, in particular in the case of denser cataracts often an overexposure can be observed in the scattering image, as a result of which the resolution suffers.

According to a third embodiment the OCT-based measurements take place in the form of B-scans along the optical axis, wherein their depth corresponds to the entire length and their width corresponds to the entire pupil of the eye. In the process, at least 2, preferably 6 and especially preferably more than 10 B scans are realized along different meridians.

Figure 3:
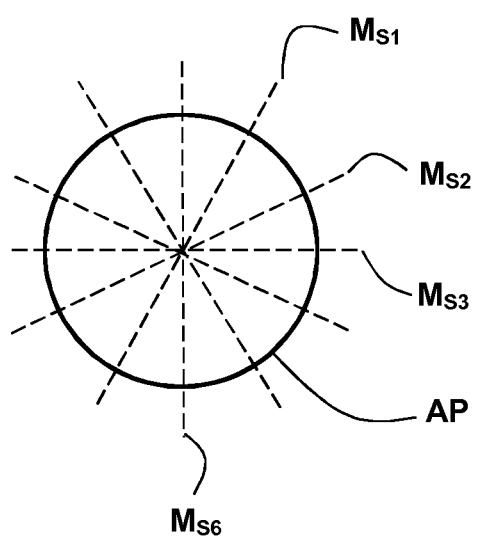
FIG. 3 shows six meridians for OCT scans to be performed.

To this end FIG. 3 shows an eye pupil AP with six meridians $M_{S1}$ through $M_{S6}$ for OCT scans to be performed. Although the meridians MS for OCT scans to be performed are evenly distributed in FIG. 3, this is not absolutely necessary. On the contrary, it is also possible to place the meridians more narrowly in the interesting regions depending on the detected cataract distributions or to carry out OCT scans in further meridians.

It goes without saying that the classification of a cataract of an eye and thus also the determination of parameters for pre-setting phaco-treatment machines become more precise, the more OCT-based measurements are realized. In particular, in this regard it is also possible to resort to a new optical tomographic method, holoscopy. Holoscopy combines the advantages of OCT and holography in medical imaging.

While optical coherence tomography (OCT) has been established for many years in medical technology, holoscopy has just been introduced. The method for 3D imaging a scattering sample, in particular for determining the spatial scattering intensity distribution S(x, y, z) of the sample is described in DE 10 2011 018 603 B3.

The short-coherent light of the swept source laser light source is directed along the optical axis into the human eye and scanned in transverse direction over the full eye pupil of about 6 mm.

In accordance with the invention, in this connection only the radiation of the swept source laser light source is detected which is scattered directly back from the boundary surfaces and from the lens volume. Radiation that is scattered directly back means the radiation which includes an angle of a maximum ±10°.

This angular region of <+/−10° correlates well with the actual anatomical symmetry of the human eye. As a rule, the optical axis of the human eye is inclined about 5° to the side of the nose.

According to a further embodiment, the OCT-based scans are analyzed using imaging technology by assessing the brightness of the individual structures.

The realized OCT scans show all structures of the relevant eye, wherein each individual structure shows different reflection and scattering degrees due to specific refractive indexes and tissue densities.

In this method, in accordance with the invention the individual segments of the OCT-based scan are given priority in the analysis with respect to the distribution of the brightness, said segments correlating directly with the local tissue density. Further, provision is made to support the diagnostic statements about the degree of hardness of the lens through additional image processing, in which along with the brightness also the inner structural features of the scattering lens ("Architecture of the Cataract") are classified and as a result, or together with the scatter intensity an estimate of the expected degree of hardness takes place.

Figure 4:
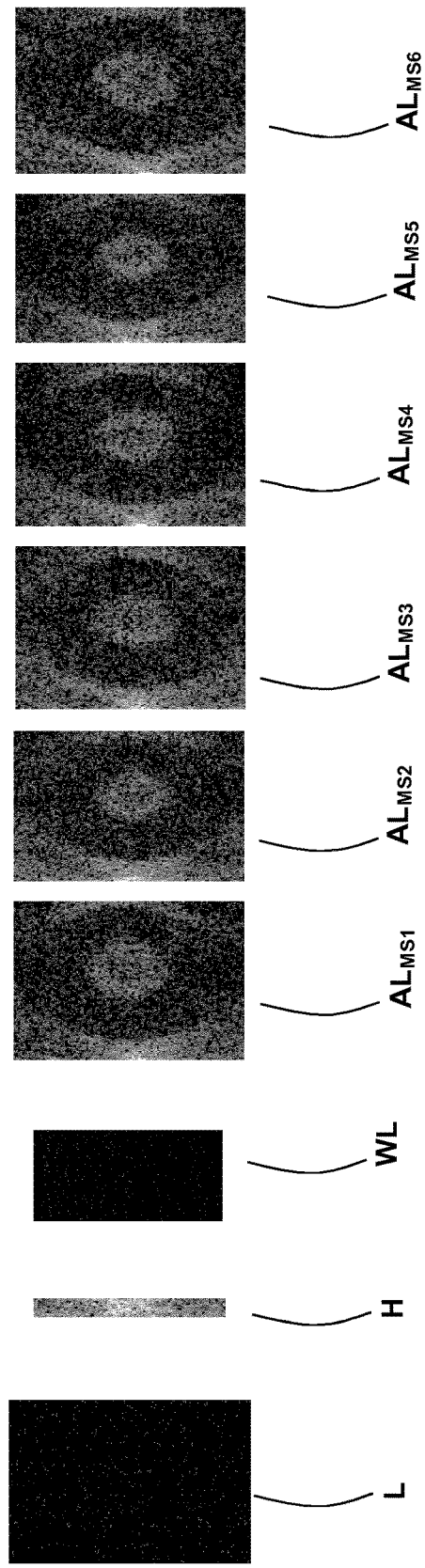
FIG. 4 shows segments of OCT scans to be analyzed performed under different meridians.

To this end FIG. 4 shows the segments to be analyzed of the OCT scan conducted under different meridians. The analysis of the individual segments shows in particular the following results from left to right:

The air L in the case of a refractive index of n=1.0 shows no scattering/reflection.

As an optical element of the eye with a defined tissue density and a higher refractive index of n=1.38 the cornea H shows a significant scattering/reflection.

The aqueous solution WL through its liquid state and a lower refractive index of n=1.34 shows a significantly lower scattering/reflection than the cornea.

The eye lens AL shows significant brightness curves that arise from the cataract degree and the opacity of the lens. The OCT-based scans of the lens along 6 evenly distributed meridians $M_{S1}$ through $M_{S6}$ are presented here. As a rule the lens has refractive indexes of from n=1.39 to n=1.41 and has differing tissue densities.

The different cataract types are assigned to different groups in dependency on their brightness values and/or structural features, said groups for which corresponding parameters are defined for pre-setting the phaco-treatment machines.

In accordance with the invention, the brightness distributions thus determined and/or the structure of the eye lens serve the purpose of classifying the cataract on the basis of comparison values. For example, this can take place in the following 3 steps:

a) soft cataract,
b) medium cataract and
c) hard cataract.

This corresponds to the following parameters for the pre-settings:

a) soft cataract—low parameters for phacoemulsification
b) medium cataract—medium parameters for phacoemulsification
c) hard cataract—high parameters for phacoemulsification However, the classification is not limited to the steps mentioned above, but rather could also take place in more than 3 steps.

According to a further embodiment, parameters for the pre-setting of phaco-treatment machines are determined from the biometric data, the local distribution and the classification of the cataract, wherein the parameters for the pre-setting of phaco-treatment machines vary correspondingly depending on the device to be used for the phaco-treatment or the technology to be applied (e.g. divide and conquer or chip).

To this end, OCT-based measurements are realized, the OCT-based scans are analyzed using imaging technology and the local distribution of the cataract is determined, the cataract is classified on the basis of comparison values and the parameters for the pre-setting of the phaco-treatment machines are determined from the local distribution and the classification of the cataract.

The parameters for the (ultrasound) phacoemulsification are in the process additionally dependent on the treatment method, the phaco-needle used (20 g/21 g/22 g) and even the technique of the attending physician.

In the case of the phacoemulsification, the eye lens is fragmented by use of a tube or needle induced by ultrasound and the debris subsequently sucked up by use of a suction rinsing device. In addition to the ultrasound energy, the most important parameters have to do with the control of the rinsing and suction pressure.

According to a further embodiment, OCT-based measurements are realized, the OCT-based scans are analyzed using imaging technology and the local distribution is determined, the cataract is classified on the basis of comparison values and parameters for the pre-setting of laser phaco-treatment devices are determined from the local distribution and classification of the cataract.

Essentially the performance parameters of the fs laser are defined as parameters for the laser-phaco, such as pulse energy, repetition rate, point spacing or type of radiation pattern and number of sectional planes.

Along with the ultrasound-based phacoemulsification, the laser-phaco method based on fs lasers is becoming increasingly important and is in widespread use in cataract surgery due to the safe cutting and an improved lens fragmentation The performance parameters of the surgical fs laser, such as pulse energy and repetition rate, are required especially for lens fragmentation, in order to be able to effectively and securely fragment the lens tissue corresponding to its optical scattering properties and the associated cataract degree.

In accordance with the invention, the OCT-based data of a prior diagnosis can be used to set the parameters for an fs laser system. If the surgical fs laser system has an integrated OCT imaging or navigation system, in addition the diagnostics can occur or can also be repeated shortly before the OP, i.e. in the operating room.

According to a further embodiment, the parameters for pre-setting the laser-phaco can be selected such that the fs laser system is used for support of the subsequent phacoemulsification.

Hence it would be possible to generate a complete workflow also for fs laser supported cataract operations and perform the fragmentation of the eye lens with the help of the fs laser in order to finally generate the correct settings for the phasoemulsification from the OCT-based biometry data prior to the operation. For this purpose, in particular the postoperative diagnostic data of the OCT imaging or navigation system integrated in the fs laser can be used to predict the setting of the phaco-treatment machine.

A special adjustment of the final settings for the phasoemulsification in the fs laser-supported cataract operation can take place by using OCT-based data of the lens after fragmentation by application of fs laser.

The inventive solution provides a method for the classification of the cataract of an eye for determining parameters for pre-setting phaco-treatment machines with which, along with keratometric measurements, in addition OCT-based measurements can be realized, the required biometric data for a phaco-treatment determined from the kerametric and OCT-based measurements, the OCT-based scan can be analyzed using imaging technology and the local distribution of the cataract determined, the cataract can be classified on the basis of comparison values and the parameters for the pre-setting of phaco-treatment machines can be determined from the biometric data, the local distribution and the classification of the cataract.

With the proposed method for classifying the cataract of an eye a simple and reliable classification and the generation of parameters for pre-setting phaco-treatment machines is possible, wherein the geometry of the respective eye is considered. Manual or automatic setting of the phaco-treatment machines makes the treatment safer and reduces the burden on the patient.

One advantage of the method can be seen in the fact that it is suitable both for the classification of the cataract of an eye for generating parameters for pre-setting of ultrasound-based as well as laser-based phaco-treatment machines.

The proposed method provides for the consideration of both the biometric data, in particular of the eye length, as well as the classified cataract data.

In the case of laser-based phaco-treatment machines, the advantage for the patient can be seen in the fact that the laser parameters (pulse energy, repletion rate, point spacing) as well as the number of sectional planes, patterns as well as pattern density are determined such that the operation can be carried out with the lowest possible laser power or light dosage.

We claim:

1. A method for classifying a cataract of an eye for determining parameters for presetting phaco-treatment instruments, comprising:
   acquiring OCT-based B-scan measurements in multiple scan orientations by application of an OCT instrument having a laser light source;
   analyzing the OCT-based B-scan measurements using computer based imaging technology;

determining a local distribution of the cataract;
classifying the cataract based on comparison values; and
determining the parameters for the pre-setting of phaco-treatment instruments from the local distribution and the classification of the cataract.

2. The method according to claim 1, further comprising:
determining required biometric data for a phaco-treatment from the OCT-based measurements;
determining the parameters for pre-setting the phaco-treatment instruments from the biometric data, the local distribution and the classification of the cataract.

3. The method according to claim 1, further comprising:
along with the OCT-based measurements, acquiring keratometric measurements;
determining biometric data for a phaco-treatment from the keratometric measurements and OCT-based measurements;
determining parameters for the pre-setting of phaco-treatment instruments from the biometric data, the local distribution and the classification of the cataract.

4. The method according to claim 1, further comprising acquiring the keratometric measurements at least one point.

5. The method according to claim 4, further comprising acquiring the keratometric measurements at least six points.

6. The method according to claim 4, further comprising acquiring the keratometric measurements at least eighteen points.

7. The method according to claim 1, further comprising acquiring the OCT-based measurements based on a swept source laser light source.

8. The method according to claim 7, further comprising utilizing the swept source laser light source such that the swept source laser light source emits short coherent light with a wavelength between 800 nm and 1100 nm.

9. The method according to claim 7, further comprising utilizing the swept source laser light source such that the swept source laser light source emits short coherent light with a wavelength of 1060 nm.

10. The method according to claim 7, further comprising utilizing the swept source laser light source such that the swept source laser light source has a spectral bandwidth between 3 nm and 260 nm.

11. The method according to claim 7, further comprising utilizing the swept source laser light source such that the swept source laser light source has a spectral bandwidth between 10 nm and 100 nm.

12. The method according to claim 7, further comprising utilizing the swept source laser light source such that the swept source laser light source has a spectral bandwidth between 20 nm and 40 nm.

13. The method according to claim 1, further comprising determining required biometric data for a phaco-treatment from the OCT-based measurements with an axial resolution <27 μm and the lateral resolution <100 μm.

14. The method according to claim 1, further comprising acquiring the OCT-based measurements in the form of B scans along the optical axis, wherein depth of the B scans corresponds to a total length of the eye and width of the B scans corresponds to an entire pupil of the eye.

15. The method according to claim 7, further comprising making the OCT-based measurements performing B scans along at least 2 different meridians.

16. The method according to claim 7, further comprising making the OCT-based measurements performing B scans along at least 6 different meridians.

17. The method according to claim 7, further comprising making the OCT-based measurements performing B scans along more than 10 different meridians.

18. The method according to claim 6, further comprising in the case of the OCT-based measurements detecting only those radiation components reflected from a boundary surface that enclose an angle of a maximum of ±10° with the visual axis of the eye.

19. The method according to claim 1, further comprising analyzing the OCT-based scans using imaging technology by assessing the brightness of individual structures.

20. The method according to claim 1, further comprising utilizing a brightness distribution thus determined of a structure of an eye lens for a purpose of classifying the cataract on a basis of comparison values.

21. The method according to claim 1, further comprising determining the classification of the cataract in the following three steps:
    soft cataract;
    medium cataract; and
    hard cataract.

22. The method according to claim 20, further comprising determining the classification of the cataract in more than three steps.

23. The method according to claim 1, further comprising acquiring the OCT-based measurements;
    further analyzing the OCT-based scans using imaging technology;
    further determining the local distribution of the cataract;
    further classifying, the cataract based on comparison values; and further determining parameters for the pre-setting of phaco ultrasound-treatment instruments or laser phaco-treatment instruments from the local distribution and the classification of the cataract.

24. The method according to claim 1, further comprising determining the parameters for the phacoemulsification additionally dependent on treatment method, a phaco needle used and on a technique of an attending physician.

25. The method according to claim 1, further comprising determining performance parameters of a femtosecond laser defined as parameters for laser- phaco, including at least one of pulse energy, repetition rate, point spacing, type of radiation pattern and number of sectional planes.

26. The method according to claim 25, further comprising selecting the parameters for pre-setting the laser-phaco such that the femtosecond laser system is used to support a subsequent phacoemulsification.

* * * * *

UNITED STATES PATENT AND TRADEMARK OFFICE
CERTIFICATE OF CORRECTION

PATENT NO. : 10,959,612 B2
APPLICATION NO. : 15/745902
DATED : March 30, 2021
INVENTOR(S) : Akhil Ramesh Kumar et al.

It is certified that error appears in the above-identified patent and that said Letters Patent is hereby corrected as shown below:

In the Specification

Column 3, Line 13, delete "," and insert --.--

Column 4, Line 1, delete "FIG. 1:" and insert --FIG. 1--

Column 4, Line 3, delete "FIG. 2:" and insert --FIG. 2--

Column 4, Line 5, delete "formed and" and insert --formed, and--

Column 8, Line 15, delete "phasoemulsification" and insert --phacoemulsification--

Column 8, Lines 20-21, delete "phasoemulsification" and insert --phacoemulsification--

Signed and Sealed this
Twenty-sixth Day of April, 2022

Katherine Kelly Vidal
*Director of the United States Patent and Trademark Office*